US008920498B2

(12) United States Patent
Buma et al.

(10) Patent No.: US 8,920,498 B2
(45) Date of Patent: Dec. 30, 2014

(54) NON-RESORBABLE MENISCUS PROSTHESIS FOR THE HUMAN KNEE JOINT

(75) Inventors: P. Buma, Nijmegen (NL); T. G. van Tienen, Nijmegen (NL)

(73) Assignee: Stichting Katholieke Universiteit, Nijmegen (NL)

( * ) Notice: Subject to any disclaimer, the term of this patent is extended or adjusted under 35 U.S.C. 154(b) by 9 days.

(21) Appl. No.: 13/696,357

(22) PCT Filed: May 6, 2011

(86) PCT No.: PCT/EP2011/002262
§ 371 (c)(1),
(2), (4) Date: Dec. 12, 2012

(87) PCT Pub. No.: WO2011/138045
PCT Pub. Date: Nov. 10, 2011

(65) Prior Publication Data
US 2013/0079877 A1 Mar. 28, 2013

(30) Foreign Application Priority Data
May 6, 2010 (EP) .................................. 10004793

(51) Int. Cl.
*A61F 2/30* (2006.01)
*A61F 2/38* (2006.01)
*A61B 17/56* (2006.01)

(52) U.S. Cl.
CPC ........... *A61F 2/30756* (2013.01); *A61F 2/3872* (2013.01); *A61B 17/562* (2013.01)
USPC ....................................................... 623/14.12

(58) Field of Classification Search
CPC .............................. A61F 2/3872; A61F 17/562
USPC ........................................................ 623/14.12
See application file for complete search history.

(56) References Cited

U.S. PATENT DOCUMENTS

| 4,344,193 | A | 8/1982 | Kenny |
| 5,092,894 | A | 3/1992 | Kenny |
| 5,171,322 | A | 12/1992 | Kenny |
| 7,641,694 | B1* | 1/2010 | Goble et al. ............... 623/18.11 |
| 2001/0039459 | A1 | 11/2001 | Stone |
| 2002/0022884 | A1 | 2/2002 | Mansmann |
| 2007/0162005 | A1* | 7/2007 | Peterson et al. ................ 606/61 |
| 2008/0195205 | A1* | 8/2008 | Schwartz ................... 623/14.12 |
| 2008/0255665 | A1 | 10/2008 | Weissberg |

FOREIGN PATENT DOCUMENTS

EP 0372811 A1 11/1989

* cited by examiner

*Primary Examiner* — David H Willse
*Assistant Examiner* — Javier Blanco
(74) *Attorney, Agent, or Firm* — Hudak, Shunk & Farine Co. LPA

(57) ABSTRACT

Meniscus prosthesis assembly having a meniscus prosthesis body made of a first biocompatible non-resorbable material and having a first end portion and a second end portion; and a first bone plug made of a second biocompatible non-resorbable material for osseous integration, the first bone plug having a first end portion and a second end portion; wherein the first end portion of the first bone plug is arranged at and operatively connected to the first end portion of the meniscus prosthesis body, and wherein the first biocompatible non-resorbable material and the second biocompatible non-resorbable material are the same or different. The assembly further comprises at least one suture, wherein the at least one suture is arranged at and operatively connected to the second end portion of the first bone plug.

12 Claims, 2 Drawing Sheets

NON-RESORBABLE MENISCUS PROSTHESIS FOR THE HUMAN KNEE JOINT

FIELD OF THE INVENTION

The The present invention relates to a non-resorbable meniscus prosthesis for the human knee joint.

BACKGROUND OF THE INVENTION

Non-resorbable meniscus prosthesis are known from for example U.S. Pat. Nos. 5,171,322 and 5092,894, the latter being a divisional application of the first. Both describe a stabilized meniscus prosthesis, comprising a body with tails attached to both ends of the body. The tails are used to fix the body in a predetermined place. U.S. Pat. No. 5,171,322 also discloses different ways to connect the tails together. In one embodiment the prosthesis may contain a porous border to allow fibrous tissue in-growth and thereby attachment to soft tissue surrounding the knee joint, e.g. synovial tissue and/or peripheral capsule. The design of the body of the meniscus prosthesis known from U.S. Pat. Nos. 5,171,322 and 5,092,894 is similar to the design disclosed in U.S. Pat. No. 4,344,193 and approaches the design of the native meniscus, however is not a copy.

A disadvantage of the meniscus prosthesis disclosed in U.S. Pat. Nos. 5,171,322 and 5,092,894 is that it is not rigidly attached to surrounding bone in the knee joint. The mobility of the meniscus prosthesis as disclosed in the cited references may cause instabilities of the meniscus when compressive stress is applied. Such compressive stresses, which already exist under normal exercise of the knee joint (e.g. standing, walking), may cause the meniscus prosthesis body to expand in a radial direction, with the risk that it extends outside the knee joint and causes instability of the knee joint.

SUMMARY OF THE INVENTION

There is a need for a non-resorbable meniscus prosthesis, made of biocompatible materials, because the available amount of allograft transplantation material (i.e. donor material) is by far not enough to satisfy the need for it. Such artificial non-resorbable meniscus prosthesis should be easy to implant and integrate well in the knee joint and being able to be loaded quickly after implantation.

It is an object of the present invention to provide a non-resorbable meniscus prosthesis assembly for the human knee joint that overcomes or at least mitigates at least part of the stated disadvantages and which at least partly satisfies the above stated requirements.

This object is achieved by providing a meniscus prosthesis assembly, comprising
- a meniscus prosthesis body made of a first biocompatible non-resorbable material and having a first end portion and a second end portion; and
- a first bone plug made of a second biocompatible non-resorbable material for osseous integration, the first bone plug having a first end portion and a second end portion;

wherein the first end portion of the first bone plug is arranged at and operatively connected to the first end portion of the meniscus prosthesis body, and wherein the first biocompatible non-resorbable material and the second biocompatible non resorbable material may be the same or different.

An advantage of a meniscus prosthesis assembly according to the present invention is that contrary to the meniscus prosthesis known from the above cited prior art, relatively shallow holes are required to accommodate the bone plugs and relatively small bore tibial channels through which the sutures may be retrieved. This may have a seriously diminishing impact on the severity of the required surgery which positively influences the comfort to the patient and may lead to possibly shorter recovery times.

The meniscus prosthesis assembly according to the present invention further comprises at least one suture, wherein the at least one suture is arranged at and operatively connected to the second end portion of the first bone plug.

The sutures may initially provide additional permanent fixation, when non-resorbable sutures are used. The function of the sutures is to temporarily fix the meniscus prosthesis assembly after surgery in order to allow osseous in-growth in a porous structure of the bone plugs which may provide permanent fixation of the meniscus prosthesis assembly.

In some embodiments the meniscus prosthesis assembly according to the present invention comprises a second bone plug for osseous integration. The second bone plug has a first end portion and a second end portion, wherein the first end portion of the second bone plug is arranged at and operatively connected to the second end portion of the meniscus prosthesis body.

A meniscus prosthesis assembly having two bone plugs may provide a more stable fixation of the meniscus prosthesis assembly after implantation in the knee joint of the human body.

Furthermore, after implantation and fixation a meniscus prosthesis assembly having two bone plugs shows a biomechanical behavior that is very similar to the behavior of a native meniscus.

In some embodiments, the second (posterior) bone plug and/or the first bone plug are fully integrated in the meniscus prosthesis body. Fully integrated in the context of this embodiment means that the second (posterior) bone plug and/or the first bone plug form a single body with the meniscus prostheses body.

In some embodiments the meniscus prosthesis assembly according to the present invention comprises the second bone plug for osseous integration and the at least one suture is arranged at and operatively connected to the second end portion of the second bone plug and/or the second end portion of the first bone plug.

In further embodiments the at least one suture has a first end portion and a second end portion and the at least one suture may be fully integrated in the meniscus prosthesis body and the second bone plug and/or the first bone plug, and wherein the first end portion of the at least one suture extends from the second end of the first bone plug and wherein the second end portion of the at least one suture extends from the second end of the second bone plug or from the second end portion of the meniscus prosthesis body.

In further embodiments, the at least one suture comprises a first suture and a second suture. The first suture is arranged at and operatively connected to the second end portion of the first bone plug and the second suture is arranged at and operatively connected to the second end portion of the second bone plug.

The first and the second sutures may be fully integrated in the meniscus prosthesis body and the second bone plug and/or the first bone plug. The first suture may extend from the second end of the first bone plug. The second suture may extend from the second end of the second bone plug or from the second end portion of the meniscus prosthesis body.

In some embodiments the meniscus prosthesis body of the meniscus prosthesis assembly according to the present invention is a copy of the native meniscus. A copy of a native meniscus may be a meniscus prosthesis body being of a standard shape and available in different sizes. Such standard prosthesis may be customized to fit the patient. It may also be possible to make an exact copy of the patients native meniscus, e.g. with a 3D-prototyping technique based on tomographic imaging techniques (e.g. CT-scans) or Magnetic Resonance Imaging. An example of a 3D-prototyping technique is rapid prototyping using for example stereo-lithography. In this technique a reservoir containing a UV-curable resin or composition is (locally) irradiated with a UV-laser according to a predetermined 3D image, in this case of a meniscus body of a patient, determined with the above mentioned imaging techniques. Upon radiation, the UV-curable composition cures locally and a solid form according to the 3D irradiation pattern is formed, which solid form is then lifted from the surrounding liquid UV-curable composition in which it is immersed. In this way a meniscus body may be directly formed or a mold may be formed according to the negative image of a meniscus body of a patient. The mold may then be used to produce a meniscus body, e.g. with a casting technique. Another example of a 3D-prototyping technique is 3D-printing which may be for example a hot melt printing technique or a printing technique with intermediate curing of a printed layer with actinic radiation, preferably UV-radiation. The 3D-printing technique may also be a combination of hot melt printing and intermediate curing with actinic radiation. Such techniques require printable biocompatible materials or precursors which are able to react or to be cured after being printed. Suitable materials for this purpose may comprise UV-curable groups or have a melting point of between 50° C. and 150° C. (for use in hot melt printing) or a combination thereof.

An advantage of these embodiments is that it provides more comfort to the patient because once the meniscus prosthesis assembly has been implanted, and the trauma has healed, the knee joint comprising the artificial meniscus, closely resembles the knee joint with the original native meniscus. The meniscus prosthesis may behave in a similar way than the original native meniscus.

An advantage of using an exact copy of a meniscus is that these embodiments allow a normal biomechanical motion pattern which may prevent damage of the implant. A (nearly) normal behavior of the implant in the knee may provide maximal pain relief.

In some embodiments the first biocompatible non-resorbable material has a tear strength of at least 100 kJ/m², preferably between 110 kJ/m² and 1000 kJ/m², more preferably between 125 kJ/m² and 750 kJ/m² and even more preferably between 150 kJ/m² and 500 kJ/m².

This parameter is measured according to ASTM D624.

In some embodiments the first biocompatible non-resorbable material has a strain at break of at least 700%, preferably between 750% and 2000%, more preferably between 800% and 1800% and even more preferably between 900% and 1500%.

In some embodiments the first biocompatible non-resorbable material (i.e. the prosthetic material) has a circumferential tensile modulus is of between 50 MPa and 200 MPa, preferably between 75 MPa and 175 MPa, more preferably between 100 MPa and 150 MPa.

In some embodiments the first biocompatible non-resorbable material has an ultimate strain (i.e. strain at the ultimate strength or $\epsilon_{max}$) of between 20 and 40% (i.e. $\epsilon_{max}$ is between 0.20 and 0.40).

In some embodiments the first biocompatible non-resorbable material has a compression modulus ($E_{compr}$) of between 25 and 150 kPa measured at a deformation rate of 0.63 mm/s. Preferably at physiological loading rates of e.g. 32%/sec (i.e. strain rate) the compression modulus is up to 8 times, preferably 2-7 times higher than the above stated values, for example up to 1.2 MPa, preferably between 0.5 and 1.0 MPa.

The above stated mechanical parameters (strain at break, tensile modulus, ultimate strain and compression modulus) are determined from stress strain curves recorded with a tensile tester (Zwick) in tensile or compression mode.

In some embodiments the first biocompatible non-resorbable material comprises a polymer. Preferably, the meniscus prosthesis body of the meniscus prosthesis assembly according to the present invention is made of a biocompatible polymeric material.

In some embodiments the biocompatible polymeric material is selected from the group comprising a hydrogel material (such as a synthetic polyacrylonitrile polymer, PVA hydrogel), elastomers, polypropylene, polyethylene, PEEK, silicon rubbers, and polyurethane carbonates, like for example trimethyl carbonate polyurethane. Preferably silicon rubbers or polyurethane carbonates are used.

Such materials together with the design of the meniscus prosthesis body provide the required properties to the meniscus prosthesis body, e.g. high tear strength, high strain at break, flexibility, high stiffness, high wear resistance.

Other examples of suitable biocompatible materials can be natural materials, such as collagen, tendon or fibre cartilage. Combinations of polymeric materials can also be used.

In some embodiments, the meniscus prosthesis body of the meniscus prosthesis assembly according to the present invention may contain a solid or porous body and comprises a porous outer rim, with pores having sizes in the range of 150 µm- 35 µm, preferably in the range of 175 µm-300 µm, more preferably in the range of 200 µm-250 µm, determined with scanning electron microscopy (SEM). The outer rim preferably has a thickness between 0.01 mm and 10 mm, more preferably between 0,1 mm and 5 mm, more preferably between 0.2 and 2 mm. The pore size and pore size distribution may be determined by making SEM images of one or more cross-sections of a body of a biocompatible non-resorbalole material made for the purpose of this invention, The SEM image will show material rich areas and areas representing pores (e.g. areas that are void of any material). The pore sizes and pore size distribution are determined by measuring the sizes of the areas representing the pores, for example by determining the equivalent circle diameter of the pores using 3 or 5 point definition method (i.e. a method which determines the diameter of a circle through 3 or 5 points on the periphery of a pore). This technique may be automated by computer aided image analysis. Because all mentioned techniques are based on the same SEM image, the results of the techniques will be the same.

In some embodiments of the present invention, the meniscus prosthesis body of the meniscus prosthesis assembly contains a solid or porous body and comprises a porous outer rim, with pores having sizes in the range of 150 µm-355 µm, preferably in the range of 175 µm-300 µm, more preferably in the range of 200 µm-250 µm, determined with mercury intrusion porosimetry. The outer rim preferably has a thickness between 0.01 mm and 10 mm, more preferably between 0.1 mm and 5 mm, more preferably between 0.2 and 2 mm. Mercury intrusion porosimetry is an analytical technique for the determination of pore size distribution and the measurement of pore volume, pore area and porosity. The operation of all mercury porosimeters is based upon the physical principle that a non-reactive, non-wetting liquid will not penetrate tine pores until sufficient pressure is applied to force its entry. The relationship between the applied pressure and the pore diameter into which mercury will intrude is given by the Washburn equation: $D=(-4\gamma\cos\theta)/P$ where P is the applied pressure, D is the pore diameter, $\gamma$ is the surface tension of the mercury (480 dyne cm−1) and $\theta$ is the contact angle between mercury and the pore wall, usually taken as 140°. Mercury intrusion porosimeters are available e.g. from MCA Services and Quantachrome UK Ltd.

An advantage of these embodiments with the porous body and the porous outer rim is that the meniscus prosthesis body will optimally integrate by tissue in-growth with surrounding soft tissues in the knee joint, and by fixation of the meniscus prosthesis body to the synovial tissue and/or peripheral capsule.

In some embodiments, the bone plugs of the meniscus prosthesis assembly according to the present invention are made of a second biocompatible non-resorbable material comprising a porous material having pore sizes in the range of 250 μ-500 μm, preferably in the range of 280 μm-450 μm, more preferably in the range of 300 μm-400 μm determined with scanning electron microscopy (SEM).

In some embodiments, the bone plugs of the meniscus prosthesis assembly according to the present invention are made of a second biocompatible non-resorbable material comprising a porous material having pore sizes in the range of 250 μm-500 μm, preferably in the range of 280 μm-450 μm, more preferably in the range of 300 μm-400 μm, determined with mercury intrusion porosimetry.

The porosity of the material may be between 25% and 85%, preferably between 50% and 80% and more preferably between 60% and 75%. This porous material can be present as an outer rim of the bone plugs, or extent through the bone plug. The porosity may be determined by Archimedes' principle.

In some embodiments the bone plugs comprise a solid body having a porous outer rim. The porous outer rim having pore sizes and a porosity in the ranges as described above. In some embodiments the bone plugs comprise a solid body provided with a porous coating. The porous coating having pore sizes and a porosity in the ranges as described above. The porosity in the context of this invention may be determined by determining the fraction for percentage) of the surface of the SEM image representing the pores, according to the previously described methods.

In some embodiments the bone plugs are made of a porous material which may be the same as or different from the material of the meniscus prosthesis body and which is preferably selected from the group comprising silicon rubbers, polyurethane carbonates. In some embodiments the first biocompatible non-resorbable material and the second biocompatible material are the same.

In some embodiments, the bone plugs are provided with a coating, preferably a coating of tricalcium-phospate.

An advantage of this embodiment is that such bone plugs support faster and relatively easy bone and tissue in-growth.

In some embodiments the meniscus prosthesis body has a wedge shaped cross section, which means that the cross-sectional area of the radial exterior is greater than that of the radial interior, with a generally constant slope there between. The meniscus prosthesis body of the meniscus prosthesis assembly according to this embodiment comprises a gliding surface, being arranged at an angle with the tibial plateau of between 20' and 45°, preferably between 22° and 40°, more preferably between 25° and 35°, determined between the lowest and highest point in the cross sectional aspect of the meniscus prosthesis body. The gliding surface comprises a smooth surface.

Due to the design and choice of materials, a meniscus prosthesis according to the present invention is flexible in use, shows good properties and offers good protection of the cartilage remaining underneath the prosthesis.

It is noted that the invention relates to all possible combinations of features described herein, particularly features recited in the claims. For example, the present invention provides a meniscus prosthesis assembly, comprising
 a meniscus prosthesis body made of a first biocompatible non-resorbable material and having a first end portion and a second end portion; and
 a first bone plug made of a second biocompatible non-resorbable material for osseous integration, the first bone plug having a first end portion and a second end portion;
wherein the first end portion of the first bone plug is arranged at and operatively connected to the first end portion of the meniscus prosthesis body, and wherein the first biocompatible non-resorbable material and the second biocompatible non-resorbable material may be the same or different, comprising a first suture and a second suture, wherein
the first suture is arranged at and operatively connected to the second end portion of the first bone plug and
the second suture is arranged at and operatively connected to the second end portion of the second bone plug,
wherein the meniscus prosthesis body comprises a porous outer rim, with pores having sizes in the range of 150-355 μm, determined with mercury intrusion porosimetry.

BRIEF DESCRIPTION OF THE DRAWINGS

This The invention will now be described in detail with reference to the following figures.

DETAILED DESCRIPTION OF THE INVENTION

Figure 1:
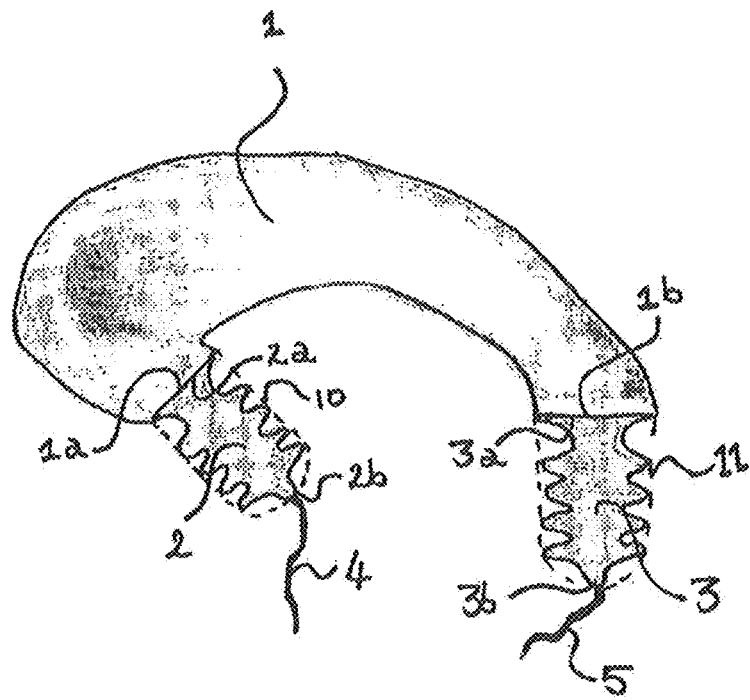
FIG. 1: Schematic representation of a meniscus prosthesis assembly according to an embodiment if the present invention.

FIG. 1 shows a schematic representation of a meniscus prosthesis assembly according to an embodiment of the present invention.

The meniscus prosthesis comprises a meniscus prosthesis body 1, which has a first end portion 1a and a second end portion 1b. The meniscus prosthesis assembly further comprises two bone plugs for osseous integration, 2 and 3. Both bone plugs have a first end portion, 2a and 3a and a second end portion, 2b and 3b, respectively. The bone plugs 2 and 3 have an overall conical shape, as illustrated by the dotted lines 10 and 11. The diameter of the bone plugs varies periodically with their length, resulting in a ribbed structure. The bone plugs of this embodiment which look like a stack of discs with a more or less oval axial cross-section, the discs being axially aligned and connected to each other.

The cone-shaped porous plugs which are continuous with the body of the implant are the key to a firm biological fixation. These porous plugs consist of a slowly or non-resorbable flexible polymer with a tricalcium-phosphate (TCP) coating which ends in a strong 0.5 mm lead to retrieve through the trans-tibial drill tunnel. The porosity of the plug is approximately between 60% and 75% and the pore size is between 300 μm and 500 μm which realizes a fast tissue and bone ingrowth. The tricalcium-phosphate coating attracts the surrounding subchondral bone, FIG. 3; 22, for a firm bony integration of the plug. The two different non-absorbable sutures from the horns will be tightened at the anterior side of the tibia to ensure a good additional fixation of the horns and hereby a stable situation for this fixation process.

The meniscus prosthesis assembly may be fixed to bone by fitting the bone plugs into holes drilled in e.g. the tibial plateau. The design of the bone plugs is such that the plugs may be fitted into holes with a smaller diameter than the maximum diameter of the plugs. The flexibility and periodically varying diameter of the bone plugs enable proper fixation of the meniscus prosthesis assembly to the bone. The porosity of the bone plugs enables in-growth of bone tissue into the bone plugs which may lead to permanent securing the meniscus prosthesis assembly.

At the second ends of both bone plugs, 2b and 3b sutures 4 and 5 are arranged to provide further fixation of the meniscus prosthesis. The sutures may be retrieved through small bore tibial tunnels. The sutures may be fixed by stitching the sutures to surrounding (soft) tissue or by knots, e.g. knotting the ends of sutures 4 and 5 together.

Figure 2:
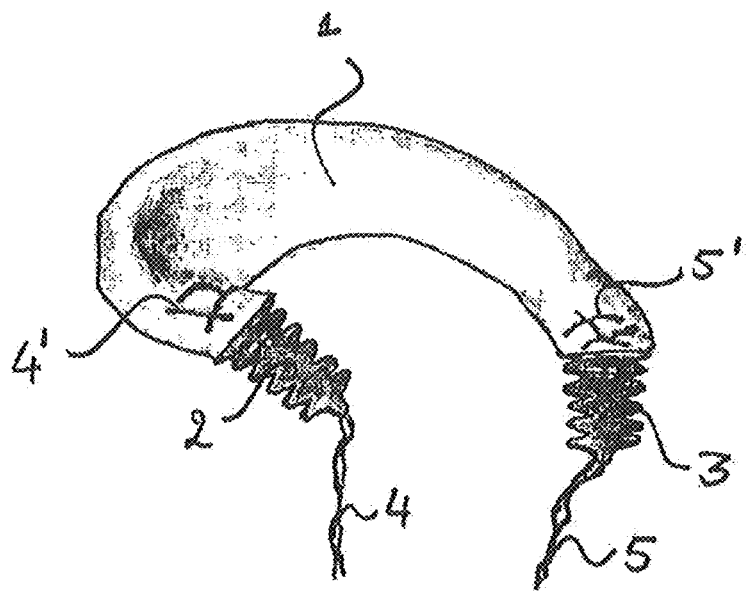
FIG. 2: Schematic representation of a meniscus prosthesis assembly according to an embodiment of the present invention.

FIG. 2 shows a schematic representation of a meniscus prosthesis assembly according to an embodiment of the present invention, wherein the sutures are not integrated but applied in the meniscus prosthesis body, 4' and 5', during surgery.

Figure 3:
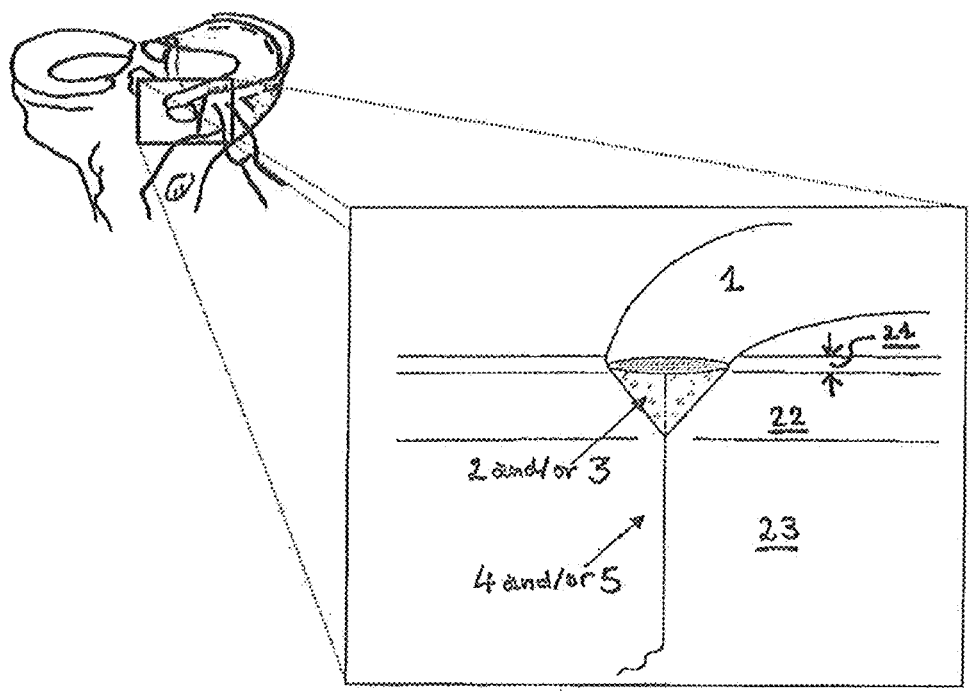
FIG. 3 Schematic representation of a lateral meniscus prosthesis assembly after placement in the human body.

FIG. 3 shows a schematic representation of a meniscus prosthesis assembly after placement in the human body. FIG. 3 also shows an enlarged schematic representation of a part of the meniscus prosthesis assembly. The enlarged part shows an end portion of the meniscus prosthesis body, also termed meniscus horn, 1. The enlarged part also shows that the porous bone plug coated with TCP [2 and 3], is integrated in the cartilage 21 and the subchondral bone 22 of the tibial plateau. The suture [4 and 5] are retrieved through a drilled tibial tunnel through the trabecular bone 23.

Figure 4:
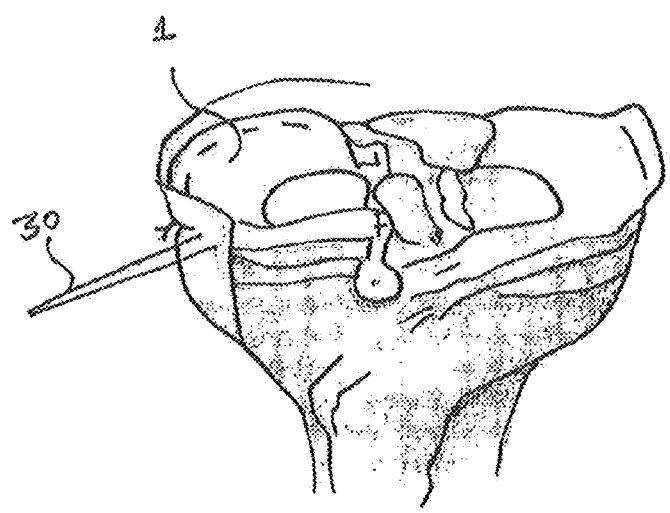
FIG. 4: Schematic representation of a medial meniscus prosthesis assembly after placement in the human body.

FIG. 4 shows a schematic representation of a medial meniscus prosthesis assembly after placement in the human body. The medial meniscus prosthesis assembly is also attached to the periphery by stitching the meniscus prosthesis body 1 with sutures 30 to the surrounding (soft) tissues.

Surgical Procedure

The procedure starts with an arthroscopy, which is an investigation of the involved compartment after confirmation of an intact anterior cruciate ligament. The whole meniscus is removed, including the peripheral rim of the meniscus to ensure optimal vascular tissue exposure (synovium). The periphery is trepanised with an spinal needle to 'vitalize' the tissue. The exact native insertions of the meniscus are determined and with the tibial aiming guide a 4 mm drill hole is created to the anterior and posterior horn fixation location. With the suture retriever the sutures on the end of the bone plugs are retrieved and pulled from the joint into the drill holes to the font of the tibia. By means of a small arthrotomy the implant is inserted to the joint. The sutures are knotted to each other after pulling the oversized plugs in the drill holes. Arthroscopically is confirmed that the plugs are completely sunk under the surface of the tibial plateau (press-fit). With 'all-inside' suture systems the posterior horn is further attached to the capsule and the mid-horn and anterior horn with 'Inside-out' sutures. At least 6 sutures are used to establish a proper stable fixation.

What is claimed is:

1. A meniscus prosthesis assembly comprising:
   a meniscus prosthesis body made of a first biocompatible non-resorbable material and having a first end portion and a second end portion, wherein the shape of the meniscus prosthesis body approximates that of the patient's native meniscus;
   a first cone-shaped bone plug made of a second biocompatible non-resorbable material for osseous integration, the first bone plug having a first end portion and a second end portion; and
   a second cone-shaped bone plug made of said second biocompatible non-resorbable material for osseous integration, the second bone plug having a first end portion and a second end portion;
   wherein the first end portion of the first bone plug is arranged at and operatively connected to the first end portion of the meniscus prosthesis body, wherein the first end portion of the second bone plug is arranged at and operatively connected to the second end portion of the meniscus prosthesis body, wherein the first bone plug and the second bone plug are fully integrated in the meniscus prosthesis body, and wherein the first biocompatible non-resorbable material and the second biocompatible non-resorbable material are the same or different,
   further comprising a first suture, wherein the first suture is arranged at and operatively connected to the second end portion of the first bone plug, and a second suture, wherein the second suture is arranged at and operatively connected to the second end portion of the second bone plug.

2. The meniscus prosthesis assembly according to claim 1, wherein the first suture has a first end portion and a second end portion and the first suture is fully integrated in the meniscus prosthesis body and the second bone plug and/or the first bone plug, and wherein the first end portion of the first suture extends from the second end of the first bone plug, and wherein the second end portion of the first suture extends from the second end of the second bone plug or from the second end portion of the meniscus prosthesis body.

3. The meniscus prosthesis assembly according to claim 1, wherein the meniscus prosthesis body is a copy of the native meniscus.

4. The meniscus prosthesis assembly according to claim 1, wherein the first biocompatible non-resorbable material has a tear strength of between 110 KJ/m$^2$ and 1000 KJ/m$^2$.

5. The meniscus prosthesis assembly according to claim 1, wherein the first biocompatible non-resorbable material has a strain at break of between 750% and 2000%.

6. The meniscus prosthesis assembly according to claim 1, wherein the first biocompatible non-resorbable material comprises a polymer, preferably selected from the group consisting of silicon rubbers and polyurethane carbonates.

7. The meniscus prosthesis assembly according to claim 1, wherein the meniscus prosthesis body comprises a porous outer rim, with pores having sizes in the range of 150-355 μm, determined with scanning electron microscopy (SEM).

8. The meniscus prosthesis assembly according to claim 1, wherein the meniscus prosthesis body comprises a porous outer rim, with pores having sizes in the range of 150-355 μm, determined with mercury intrusion porosimetry.

9. The meniscus prosthesis assembly according to claim 1, wherein the second biocompatible non-resorbable material comprises a porous material having pore sizes in the range of 250-500 μm, determined with scanning electron microscopy (SEM).

10. The meniscus prosthesis assembly according to claim 1, wherein the first biocompatible non-resorbable material and the second biocompatible non-resorbable material are the same.

11. The meniscus prosthesis assembly according to claim 1, wherein the bone plugs are provided with a tricalcium-phosphate coating.

12. The meniscus prosthesis assembly according to claim 1, wherein the meniscus prosthesis body comprises a gliding surface being arranged at an angle with a tibial plateau of between 20° and 45°.

* * * * *